US009263689B2

(12) United States Patent  
O'Carroll et al.

(10) Patent No.: US 9,263,689 B2  
(45) Date of Patent: Feb. 16, 2016

(54) ORGANIC OPTOELECTRONIC DEVICES INCORPORATING PLASMONIC ELECTRODES

(71) Applicant: Rutgers, The State University of New Jersey, New Brunswick, NJ (US)

(72) Inventors: Deirde M. O'Carroll, Metuchen, NJ (US); Christopher E. Petoukhoff, Highland Park, NJ (US); Divya Vijapurapu, Monmouth Junction, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 5 days.

(21) Appl. No.: 14/180,216

(22) Filed: Feb. 13, 2014

(65) Prior Publication Data

US 2014/0225091 A1   Aug. 14, 2014

Related U.S. Application Data

(60) Provisional application No. 61/764,374, filed on Feb. 13, 2013.

(51) Int. Cl.

| H01L 51/00 | (2006.01) |
|---|---|
| H01L 51/44 | (2006.01) |
| H01L 51/52 | (2006.01) |
| H01L 51/42 | (2006.01) |
| G01N 33/58 | (2006.01) |
| H01L 31/0224 | (2006.01) |

(52) U.S. Cl.  
CPC ............ *H01L 51/441* (2013.01); *G01N 33/587* (2013.01); *H01L 31/022425* (2013.01); *H01L 51/42* (2013.01); *H01L 51/447* (2013.01); *H01L 51/5209* (2013.01); *H01L 51/5221* (2013.01); *H01L 51/5225* (2013.01); *H01L 51/0036* (2013.01); *H01L 51/0047* (2013.01); *H01L 51/4253* (2013.01); *Y02E 10/549* (2013.01)

(58) Field of Classification Search  
CPC ................. G01N 33/587; H01L 51/42; H01L 2251/5369; H01L 31/022425; H01L 51/5206  
USPC ................................ 257/40, 91, 99, 103, 448  
See application file for complete search history.

(56) References Cited

U.S. PATENT DOCUMENTS

| 2011/0109821 A1* | 5/2011 | Tang et al. ...................... 349/32 |
| 2011/0109845 A1* | 5/2011 | Tang et al. ...................... 349/88 |
| 2011/0186119 A1* | 8/2011 | Atwater et al. ............... 136/256 |

* cited by examiner

*Primary Examiner* — Minh-Loan Tran  
(74) *Attorney, Agent, or Firm* — Fox Rothschild LLP (57) ABSTRACT

An organic optoelectronic device that includes a substrate and a plurality of structures disposed thereon, the structures include: (a) a first electrode; vertically separated from (b) a second electrode by (c) an electrode gap that includes an organic photoactive layer disposed within the gap, wherein one of the electrodes includes a plurality of plasmonic nanopores or metal nanostructures, wherein the nanostructures project towards the electrode gap and the metal is selected from gold, aluminum, silver, calcium, copper, and nickel is presented.

17 Claims, 2 Drawing Sheets

ORGANIC OPTOELECTRONIC DEVICES INCORPORATING PLASMONIC ELECTRODES

CROSS-REFERENCE TO RELATED APPLICATIONS

This application claims the benefit of U.S. Provisional Application No. 61/764,374, filed Feb. 13, 2013, the contents of which are hereby incorporated by reference in their entirety.

GOVERNMENT LICENSE RIGHTS

The present invention was made, at least in part, with government support under grant numbers DMR-1309459 and 0903661 awarded by the National Science Foundation. The government has certain rights in the invention.

BACKGROUND

Light is a wonderful means of transmitting energy and information. More solar light energy reaches our planet every hour than all of humankind consumes in one year. Much progress has been made in the field of photovoltaics in order to try to tap into this vast reservoir of energy, but further improvements in the technology are still necessary in order to expand our ability to harvest solar energy. Regarding the reverse process (of light harvesting)—light emission, an enormous source of wasted energy comes from our lighting and display applications—one of the largest percentage of battery consumption on most smartphones or tablets is attributed to the display. Great strides are necessary to improve optoelectronic devices and integrated devices used for light harvesting and light emission.

Organic-based optoelectronic devices, such as organic light emitting diodes (OLEDs) and organic photovoltaics (OPVs or organic solar cells) are not as efficient as their inorganic counterparts, and they tend to degrade more rapidly when left in air. The potential advantages of organic optoelectronic devices are large enough to motivate researchers across the globe to try to improve the efficiency, lifetime, and cost of these devices.

SUMMARY

In one aspect, the present disclosure is directed to an organic optoelectronic device that includes a substrate and a plurality of structures disposed thereon, the structures include: (a) a first electrode; vertically separated from (b) a second electrode by (c) an electrode gap that includes an organic photoactive layer disposed within the gap, wherein one of the electrodes includes a plurality of plasmonic metal nanostructures, wherein the nanostructures project towards the electrode gap and the metal is selected from gold, aluminum, silver, calcium, copper, and nickel.

In one embodiment, the first electrode is an anode that includes a plurality of plasmonic metal nanostructures and is disposed closer to the substrate than the second electrode, which is a cathode. In another embodiment, the first electrode is a cathode that includes a plurality of plasmonic metal nanostructures and is disposed closer to the substrate than the second electrode, which is an anode.

In one aspect, the plurality of plasmonic metal nanostructures further includes a native metal oxide coating layer. In one aspect, the native metal oxide coating layer is selected from CuO, NiO, $Ag_2O$, and $Au_2O_3$. In another aspect, the native metal oxide coating layer includes a thickness from about 1 nm to about 5 nm. In yet another aspect, the plurality of plasmonic metal nanostructures further includes a metal oxide coating layer. In one aspect, the metal oxide coating layer is selected from ZnO and $TiO_2$.

In one aspect, the plurality of nanostructures includes a nanorod array, a nanocone array, a nanoparaboloid array, a nanoscale grating, or a nanopillar array. In another aspect, at least one of the nanostructures includes a diameter ranging from about 10 nm to about 200 nm. In yet another aspect, at least one of the nanostructures includes an aspect ratio ranging from about 0.3 to about 5.

In one aspect, the organic photoactive layer includes a conjugated organic polymer. In another aspect, the conjugated organic polymer is selected from poly(3-hexylthiophene) (P3HT); poly[N-9'-heptadecanyl-2,7-carbazole-alt-5,5-(4',7'-di-2-thienyl-2',1',3'-benzothiadiazole)] (PCDTBT); poly({4,8-bis[(2-ethylhexyl)oxy]benzo[1,2-b:4,5-b']dithiophene-2,6-diyl}{3-fluoro-2-[(2-ethylhexyl)carbonyl]thieno[3,4-b]thiophenediyl}) (PTB7); poly(9,9-di-n-octylfluorenyl-2,7-diyl) (PFO); poly[(9,9-di-n-octylfluorenyl-2,7-diyl)-alt-(benzo[2,1,3]thiadiazol-4,8-diyl)] (F8BT); and poly[2-methoxy-5-(2-ethylhexyloxy)-1,4-phenylenevinylene] (MEH-PPV). In another aspect, a fullerene derivative is combined with a conjugated organic polymer absorber, wherein the fullerene derivative is selected from phenyl-C61-butyric acid methyl ester ($PC_{60}BM$); phenyl-C71-butyric acid methyl ester ($PC_{70}BM$); and combinations thereof.

In one aspect, an additional layer is disposed in the electrode gap. In another aspect, the additional layer is selected from poly(3,4-ethylenedioxythiophene):poly(styrenesulfonate) (PEDOT:PSS); $MoO_3$; ZnO; and $TiO_2$.

Also disclosed is an organic optoelectronic device that includes a substrate and a plurality of structures disposed thereon, where the structures include: (a) a first electrode; vertically separated from (b) a second electrode by (c) an electrode gap that includes an organic photoactive layer disposed within the gap, wherein one of the electrodes includes a plurality of plasmonic nanopores disposed in a surface of the electrode that is positioned towards the electrode gap and the metal is selected from gold, aluminum, silver, calcium, copper, and nickel.

The present disclosure also includes an article that includes an organic optoelectronic device disclosed herein, wherein the article is selected from an organic light-emitting diode, an organic solar cell, an optically pumped laser, and an indirectly electrically pumped laser.

DETAILED DESCRIPTION

In accordance with the present disclosure, organic optoelectronic devices with increased efficiency that incorporate plasmonic electrodes are described. Accordingly, in one aspect, the present disclosure provides an organic optoelectronic device that includes a substrate and a plurality of structures disposed thereon, where the structures include: (a) a first electrode; vertically separated from (b) a second electrode by (c) an electrode gap that includes an organic photoactive layer disposed within the gap, wherein one of the electrodes includes a plurality of plasmonic metal nanostructures, wherein the nanostructures project towards the electrode gap and the metal is selected from gold, aluminum, silver, calcium, copper, and nickel. In another aspect, the metal is selected from gold, copper, and nickel.

Also provided is an organic optoelectronic device that includes a substrate and a plurality of structures disposed thereon, where the structures include: (a) a first electrode; vertically separated from (b) a second electrode by (c) an electrode gap that includes an organic photoactive layer disposed within the gap, wherein one of the electrodes includes a plurality of plasmonic nanopores disposed in a surface of the electrode that is positioned towards the electrode gap and the metal is selected from gold, aluminum, silver, calcium, copper, and nickel. As used herein, the term "nanopores" refers to nanoscale pores in a thin metal film, wherein the pores can have varying geometries.

As used herein, the term "plasmonic" includes nanopores in a metal or nanostructures of metals (typically noble metals such as, for example, silver, gold, and copper) that are able to support surface plasmon resonances at visible light frequencies. These surface plasmon resonances can couple to visible light, allowing for enhancement of near- or far-electromagnetic fields.

Figure 1:
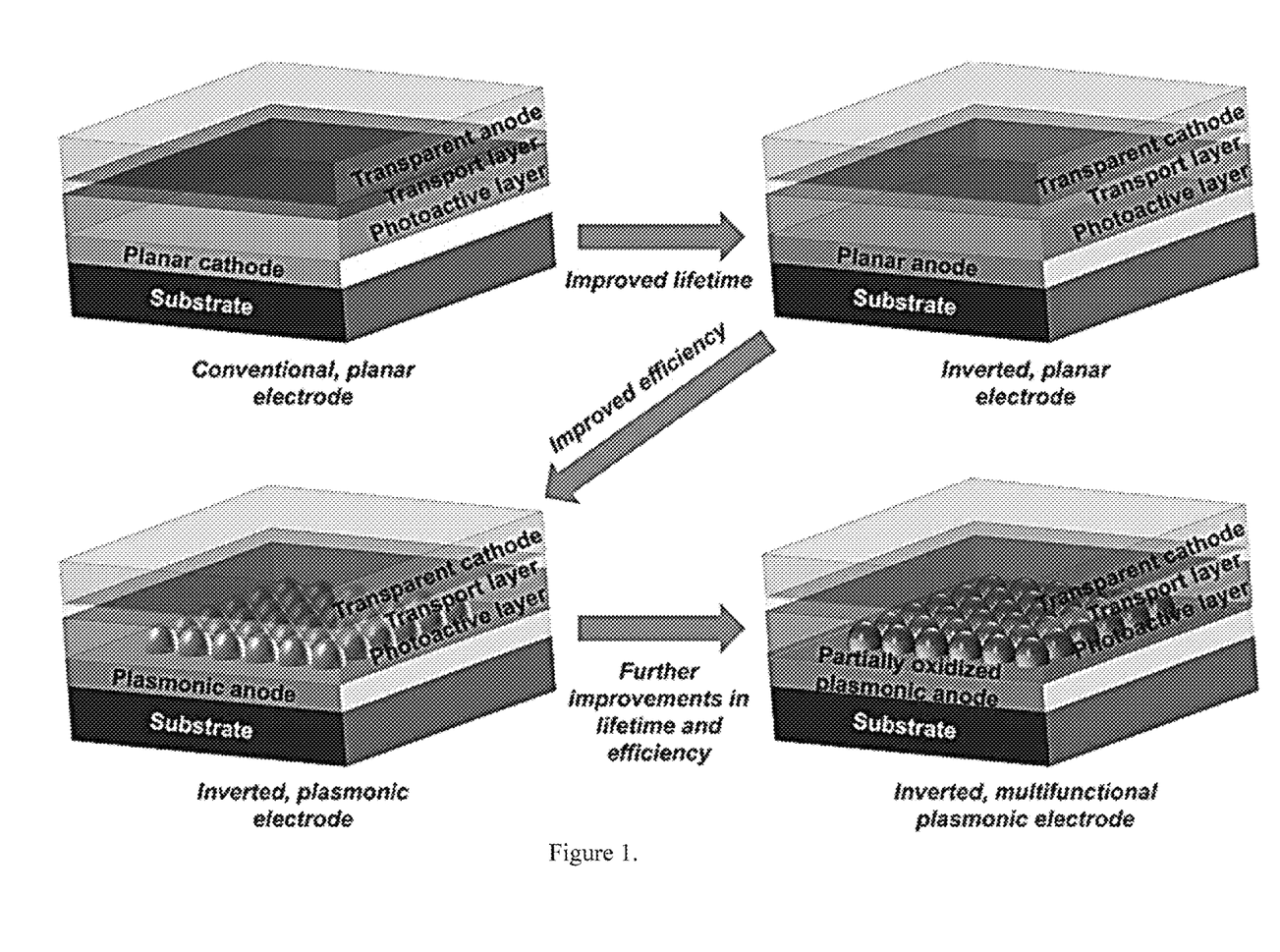
FIG. 1 is a depiction of various planar and plasmonic electrodes.

In one aspect, the first electrode is an anode that includes a plurality of plasmonic metal nanostructures and is disposed closer to the substrate than the second electrode, which is a cathode. (FIG. 1). In another aspect, the first electrode is a cathode that includes a plurality of plasmonic metal nanostructures and is disposed closer to the substrate than the second electrode, which is an anode.

Suitable substrates for the present devices include any substrates known in the art to be useful for constructing optoelectronic devices. Preferred substrates include, but are not limited to, glass and silicon.

In one aspect, the plurality of plasmonic metal nanostructures further includes a metal oxide coating layer. Exemplary methods for forming the metal oxide coating layer include, but are not limited to, atomic layer deposition and pulsed laser deposition. In another aspect, the metal oxide coating layer is a native metal oxide coating layer. Exemplary methods for forming the native metal oxide coating layer include, but are not limited to, thermal oxidation, electrochemical oxidation, and exposure to oxygen plasma.

In one aspect, preferably when the optoelectronic device is an inverted device (i.e. the anode includes a plurality of plasmonic metal nanostructures), the native metal oxide coating layer is selected from CuO, NiO, $Ag_2O$, and $Au_2O_3$. In another aspect, preferably when the optoelectronic device is a conventional device (i.e. the cathode includes a plurality of plasmonic metal nanostructures), the metal oxide coating layer is selected from ZnO and $TiO_2$. In yet another aspect, the metal oxide coating layer has a thickness from about 1 nm to about 5 nm, or any increment in between (e.g. 1 nm, 2 nm, 3 nm, 4 nm, 5 nm, etc.).

Exemplary methods to prepare the plasmonic metal nanostructures on the electrodes include template-based fabrication, nanoimprint lithography, dealloying, and thermally-assisted de-wetting of metal films. In one aspect, the plurality of nanostructures includes a nanorod array, a nanocone array, a nanoparaboloid array, a nanoscale grating, or a nanopillar array.

As used herein, the phrase "nanorod array" refers to an array of vertically-oriented cylinders with rounded ends. The phrase "nanocone array" refers to an array of vertically-oriented conical structures with the apex of the cone pointing towards the electrode gap. The phrase "nanoparaboloid array" refers to an array of vertically-oriented inverted parabolas rotated about their axes of symmetry. The phrase "nanoscale grating" refers to an array of parallel trenches and ridges. The phrase "nanopillar array" refers to a periodic array of vertically-oriented boxes.

In one aspect, at least one of the nanostructures in the array or at least one of the nanopores includes a diameter ranging from about 10 nm to about 200 nm, in any increment in between. In another aspect, at least one of the nanostructures or nanopores includes an aspect ratio ranging from about 0.3 to about 5, or any increment in between.

The organic photoactive layer can include any suitable organic photoactive material. Suitable materials include, but are not limited to, light absorbers and light emitters. In one aspect, the organic photoactive layer includes a conjugated organic polymer. Exemplary absorbers include polythiophene and polycarbazole derivatives, preferably, poly(3-hexylthiophene) (P3HT); poly[N-9'-heptadecanyl-2,7-carbazole-alt-5,5-(4',7'-di-2-thienyl-2',1',3'-benzothiadiazole)] (PCDTBT), and poly({4,8-bis[(2-ethylhexyl)oxy]benzo[1,2-b:4,5-b']dithiophene-2,6-diyl}{3-fluoro-2-[(2-ethylhexyl)carbonyl]thieno[3,4-b]thiophenediyl}) (PTB7). Exemplary emitters include polyfluorene and poly(phenylene vinylene) derivatives, preferably, poly(9,9-di-n-octylfluorenyl-2,7-diyl) (PFO); poly[(9,9-di-n-octylfluorenyl-2,7-diyl)-alt-(benzo[2,1,3]thiadiazol-4,8-diyl)] (F8BT); and poly[2-methoxy-5-(2-ethylhexyloxy)-1,4-phenylenevinylene] (MEH-PPV). In another aspect, the device further includes a fullerene derivative combined with a conjugated polymer absorber, wherein the fullerene derivative is selected from phenyl-C61-butyric acid methyl ester ($PC_{60}BM$); phenyl-$C_{71}$-butyric acid methyl ester (PC70BM); and combinations thereof.

In one aspect, the device further includes an additional layer disposed in the electrode gap. Exemplary additional layers include, but are not limited to, one or more hole-transport layers (e.g. an additional conjugated polymer layer) and one or more electron-transport layers (e.g. an additional metal oxide). Preferably, the additional layer is selected from poly(3,4-ethylenedioxythiophene):poly(styrenesulfonate) (PEDOT:PSS); $MoO_3$; ZnO; and $TiO_2$.

Also presented is an article that includes an organic optoelectronic device disclosed herein, wherein the article is selected from an organic light-emitting diode, an organic solar cell, an optically pumped laser, and an indirectly electrically pumped laser. In one aspect, when the article is a laser, the device includes a first electrode that includes a plurality of nanostructures disposed on a substrate, with a second substrate ("superstrate") vertically separated from the first electrode by an electrode gap. The electrode gap includes a photoactive layer that includes an emissive conjugated polymer with a high gain coefficient that is able to undergo stimulated emission upon either optical (e.g. a different light source) or electrical excitation.

The modifier "about" is used herein to indicate that certain preferred operating ranges, such as ranges for molar ratios for reactants, material amounts, and temperature, are not fixedly determined. The meaning will often be apparent to one of ordinary skill. Where guidance from the experience of those of ordinary skill is lacking, guidance from the context is lacking, and where a more specific rule is not recited below, the "about" range shall be not more than 10% of the absolute value of an end point or 10% of the range recited, whichever is less.

The devices and methods of the present invention are further illustrated by the examples below. These examples serve only to illustrate the invention and should not be interpreted as limiting the scope of the invention in any way, since further modifications encompassed by the disclosed invention will be apparent to those skilled in the art. All such modifications are deemed to be within the scope of the invention as defined in the present specification and claims.

EXAMPLES

Example 1

General Template-Based Fabrication Method

Glass substrates were cut and cleaned by sonicating in detergent and isopropanol, each for 15 minutes, then soaking in a mixture of HCl and ethanol (1:1) for 15 minutes, rinsing in DI water, and drying with a stream of compressed air. An adhesion layer (5 nm Cr) followed by the base metal film were thermally evaporated onto the cleaned glass substrate at a rate less than 0.1 nm/s.

Anodic aluminum oxide (AAO) nanotemplates (Synkera Technologies, Inc.) of varying pore diameters having aluminum oxide thickness of ~500 nm (coated on both sides of a thin aluminum foil, see Figure) served as the templates. The back of the nanotemplate and ~2 mm rim on the front of the nanotemplate were coated with epoxy. Once dried, the top aluminum oxide layer was etched using NaOH (3 M, aq.) for 20 min., then the nanotemplates were rinsed with fresh DI water thrice.

The nanotemplates were floated on a bath of $FeCl_3$ (250 aq.) for 2 h. to etch the aluminum layer. After rinsing with DI water thrice, the nanotemplates were immersed in a $H_3PO_4$ (5% w/w, aq.) bath, freshly prepared, which was held at 30° C. for 45-50 min. in order to remove the barrier layer and widen the pores of the AAO nanotemplate. The nanotemplates were rinsed with DI water thrice, then soaked in acetone for 10 minutes, followed by 4 fresh acetone baths for 5 min. each, then 1 ethanol and 1 isopropanol bath for 5 min. each in order to ensure complete removal of the epoxy.

Figure 2:
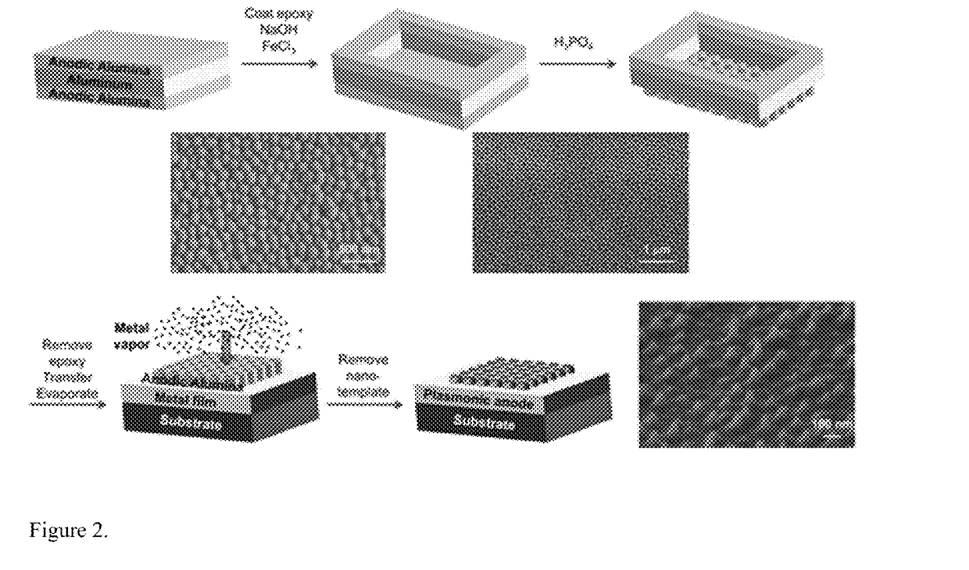
FIG. 2 is a schematic depiction of the fabrication of a plasmonic electrode along with SEM images of the plasmonic nanostructures.

Once fully etched, the nanotemplates were transferred to the metal films, with the etched-side up, and the aluminum oxide was cut off of the handle. The same metal that was used for the base metal film was evaporated through the pores of the nanotemplate. The height of the nanoparticles was controlled by the evaporation time, which was monitored using a quartz microbalance; the diameter of the particles was controlled by diameter of the pores. After evaporation through the pores, the samples were immersed under a stream of isopropanol to remove the AAO nanotemplate. The samples were then dried using compressed air, and stored in inert/dry atmosphere until further characterization or the subsequent sample preparation steps. Using this technique, nanoparticles having a paraboloidal structure were fabricated of varying heights (see SEM image in FIG. 2).

Example 2

Fabrication of Ag Nanoparticle Arrays

AgNPs were fabricated on either Si or Ag substrates by thermal evaporation of Ag through 600-nm-thick nanoporous anodic alumina (AAO) masks. The nanoporous alumina masks were fabricated from as prepared AAO/Al/AAO nanotemplates purchased from Synkera, Inc. which consisted of ~600 nm of AAO (55 nm pore size) on both sides of an aluminum film (10 mm×10 mm).

To prepare AAO masks for AgNP fabrication, first, one side of the AAO/Al/AAO was coated with a protective epoxy and the rim of the other side was also coated in epoxy. AAO was etched from the exposed side of the AAO/Al/AAO template using NaOH solution (3 M, 30 min). Subsequently, the Al was etched completely using FeCl3 solution (200 g/L; 2-5 h) exposing the barrier layer of the remaining AAO film. After thorough rinsing with deionized water, the barrier layer was etched using H3PO4 (5%; 55 min). Finally, the epoxy was removed by repeated immersion in acetone resulting in a through-hole AAO mask. Subsequently, an AAO mask was transferred to a Si or Ag-coated substrate and 60 nm of Ag was thermally evaporated through the mask. After thermal evaporation the mask was peeled off/delaminated from the substrate by immersing in water or ethanol, leaving an AgNP array on the underlying substrate.

The size and structure of the AgNPs was subsequently observed by scanning electron microscopy. The resulting AgNPs had a distribution of sizes on the substrate due to shadowing by the AAO mask during thermal evaporation, and nonuniform coverage of the mask on the underlying substrate prior to evaporation. The height of the nanoparticles was equal to or less than the thickness of the thermally evaporated metal layer.

Example 3

Thin Film Preparation

P3HT:PCBM thin-film layers were prepared by spin coating from solution onto the Si or Ag substrate with/without the AgNP array. The solution was prepared by adding regioregular P3HT (10 g/L, Alfa Aesar) and PCBM (10 g/L, Aldrich) to chlorobenzene and heating the mixture at 45° C. for 10 min. Solutions were stirred overnight and heated to 60° C. prior to spin coating to ensure P3HT and PCBM were fully dissolved and to facilitate homogeneous coating of the substrate. Spin coating was carried out by dispensing 20 μL of the solution onto the spinning substrate 6,000 rpm for 60 s. This yielded film thicknesses of approximately 100 nm.

Example 4

Optical Characterization

A Nikon Optiphot 66 optical microscope was used to locate AgNP regions. Dark-field and bright-field images were taken of these regions at various magnifications with a color camera. Dark-field and bright-field spectra were collected using an Andor Shamrock SR303i imaging spectrometer. Light from each nanoparticle region was collected with a 20× microscope objective and the image was directed into the imaging spectrometer [Andor Solis software was used to specify the desired binning (40 pixels), exposure time and number of accumulations]. A particular nanoparticle region was selected by imaging through the entrance slit of the spectrometer (an entrance slit width of 250 μm selected~5 μm of the sample), and the height of each region was 40 pixels.

To collect a bright-field reflection spectrum of the selected region an exposure time of 2 s was employed for 30 accumulations (lamp excitation power of 25 W). Dark-field reflected-light spectra of the selected region were acquired by inserting an opaque stop in the excitation lamp light path, opening the field and aperture diaphragms, and by using an exposure time of 20 s for six accumulations and maximum lamp intensity (50 W). Background spectra were collected under the same conditions at nearby locations of the substrate that did not contain nanoparticles to account for stray and non-nanoparticle background light contributions.

Example 5

Back-Scattered Light Spectra

To determine how the presence of P3HT:PCBM and AgNPs modified back-scattered light spectra of a sample, dark-field reflected light spectra of sample regions with and without a P3HT:PCBM layer and with and without a AgNP array were acquired under the conditions described above.

To determine the change in back-scattered light spectra due to AgNPs on Si or Ag, the dark-field spectrum of the sample region without a AgNP array was subtracted from the darkfield spectrum of the sample region with an AgNP array. The result was then divided by the dark-field reflected light spectrum of a diffuse Spectralon™ reflector to obtain the back-scattered light spectrum arising from the presence of the AgNP array. To obtain the back-scattered light spectrum arising from an AgNP array with a P3HT:PCBM coating, the darkfield reflected light spectrum of a P3HT:PCBM layer on a planar substrate region was subtracted from that of a P3HT:PCBM coated substrate region with the AgNP array. The result was then divided by the darkfield reflected light spectrum of the diffuse reflector, as before.

Example 6

Extinction Spectra

To calculate extinction and observe how it was affected by the presence of P3HT:PCBM and AgNPs, bright-field reflected light spectra of samples with and without a layer of P3HT:PCBM and with and without a AgNP array were obtained. A bright-field reflected light spectrum of the halogen lamp excitation was also obtained using a planar, unprocessed Ag film. All bright-field reflected light spectra of the unprocessed planar Ag film; processed planar Ag film region (near the AgNP array region, i.e., processed at the same time as the AgNP array region); AgNP array region on a planar Ag film (AgNP/Ag); P3HT:PCBM thin film on the same "processed" planar Ag film region as before (P3HT:PCBM/Ag); P3HT:PCBM thin film on the same AgNP/Ag region as before (P3HT:PCBM/AgNP/Ag)] were baseline corrected to remove the contribution from the noise prior to the extinction calculations. The baselined bright-field reflected light spectra of the processed planar Ag, AgNP/Ag, P3HT:PCBM/Ag, and P3HT:PCBM/AgNP/Ag sample regions were then divided by the baselined brightfield reflected light spectrum of the unprocessed planar Ag film, thus calculating reflectance relative to an unprocessed planar Ag film. To obtain extinction, the reflectance relative to a planar Ag film was subtracted from 1.

Example 7

Electromagnetic Simulations

Full-field three-dimensional finite-difference-time domain (FDTD) electromagnetic simulations were carried out using software from Lumerical, Inc. The fully complex and dispersive optical constants of silver, P3HT:PCBM, and silicon were employed. A mesh size of 3 nm was used for all simulations. To simulate back-scattered light, a total-field scattered field plane wave source was used to separate scattered light from total electromagnetic fields in the structure under study. A frequency-domain power monitor was placed above the structure and transmitted power was plotted as a function of wavelength. To simulate absorption, power absorbed was integrated over a given material and plotted as a function of wavelength. For simulations containing nanoparticles, one AgNP was located in the simulation area and periodic boundary conditions were employed to simulate an array of discrete nanoparticles with similar internanoparticle spacing to that determined from experimental averages (i.e., ~80 nm).

Light scattering and extinction from silver nanoparticle arrays fabricated on silicon and on silver substrates as a function of size and the degree of substrate contact, both with and without organic conjugated polymer:fullerene blend thin-film coatings were characterized. There was a notable (>200 nm) red-shift observed in the wavelength of back-scattered light from the silver nanoparticles on silicon as a function of increasing nanoparticle diameter (from 20 to 80 nm). When the organic layer was applied to the silver nanoparticles on silicon, back-scattering intensity from the nanoparticles was reduced and shifted to wavelengths near the absorption edge of the conjugated polymer where the refractive index was large. This indicated that a significant fraction of backscattered light from the silver nanoparticles was absorbed by the conjugated polymer material and/or was forward-scattered into the silicon substrate to a greater degree than for uncoated silver nanoparticles on silicon. Theoretical electromagnetic simulations confirmed that light scattered by the silver nanoparticles resulted in absorption enhancements in both the organic conjugated polymer:fullerene and silicon layers but only in different wavelength ranges. Additionally, the degree of contact between the silver nanoparticle and the silicon substrate had a significant effect on back- and forward-scattering and the degree of absorption enhancement in the hybrid organic/inorganic films. When silver nanoparticles were fabricated on reflective silver substrates, a significant intensity enhancement and red-shift of back-scattered light occurred at the absorption edge of the conjugated polymer upon organic layer coating. This was attributed to a red-shifted transverse nanoparticle surface plasmon resonance due to the large and strongly dispersive refractive index of the conjugated polymer at its absorption edge.

Example 8

Performance Parameter Calculations Device Setup for a Computational Comparison For typical conventional bulk-heterojunction organic photovoltaic (BHJ-OPV) devices, indium-tin oxide (ITO) serves as the transparent anode, PEDOT:PSS serves as the hole transfer layer (HTL), and P3HT blended with PCBM is used as the active layer. The P3HT:PCBM blend system has been extensively studied and was used as a model system for studying changes to the BHJ-OPV device structure other than the active layer. A metal cathode, with or without a metal oxide or fluoride electron transfer layer (ETL), completes the device stack.

For the inverted configuration, the bare or HTL-coated metal electrode served as the anode and ZnO replaced PEDOT:PSS as the ETL, making ITO the cathode. In addition to the conventional and inverted device configurations defined above, we studied three possible cases at the metal electrodes defined as: (1) bare metal electrode; (2) bare low work function metal bilayer electrode; and (3) metal oxide/fluoride-coated metal electrode. The 6 bare metal electrodes studied were Ag, Al, Cu, Au, Pd, and Ni; the 3 bare low work function metal bilayer electrodes studied were Ba/Al, Ca/Al, and Mg/Ag; all 9 of these metal electrode types will be referred to as the bare metal electrodes unless otherwise noted. The 6 coated metal electrodes studied were LiF/Al and ZnO/Al as n-type coatings; NiO/Ni, Ag$_2$O/Ag, CuO/Cu as p-type native metal oxide coatings, and MoO$_3$/Al as a standard p-type coating.

For each electrode configuration, the thickness of the ITO was 100 nm, and the total metal electrode thickness was kept at 200 nm, ensuring that it was optically thick. The thickness of the front interfacial layers (IFLs, here defined as the HTL PEDOT:PSS for the conventional devices and the ETL ZnO for the inverted devices) and that of the P3HT:PCBM layers were optimized to be 10 nm and 240 nm, respectively. For bare metals, the metal thickness was 200 nm; for the bare low work function bilayer metal electrodes, 25 nm of the low work function metal was supported by 175 nm of Al (for Ba and Ca) or Ag (for Mg) in keeping with typical experiments involving these metals in BHJ-OPVs. For the coated metal electrodes, the thickness of the oxide/fluoride was 2 nm, and the metal was 198 nm. The thickness of the coating was chosen to modify the electrode work functions without significantly changing the optical properties of the electrode.

For conventional devices, metals and n-type coatings with work functions equal to or smaller in magnitude than the LUMO energy of PCBM were expected to form ohmic contacts at the cathode. LiF and ZnO have been extensively studied for conventional BHJ-OPVs, and are known to form ohmic contacts to PCBM. Although the work function of ZnO is typically cited between 4.1 and 4.4 eV, it was expected to have a large interface dipole that reduced the energetic offset between the LUMO of PCBM and the workfunction of ZnO to nearly zero; thus the work-function of ZnO is taken to be equivalent to the LUMO of PCBM (4.0 eV). Metals or metal oxides with workfunctions larger in magnitude than the LUMO of PCBM can introduce an energy loss for electrons, $\psi_e$, collected from PCBM, which has previously been referred to as a barrier to electron injection, but barriers should not exist for an electron being collected by a high work function electrode.

For inverted devices, metals and p-type metal oxides with work-functions equal to or larger in magnitude than the HOMO energy of P3HT are expected to form ohmic contacts at the anode, whereas metals or metal oxides with workfunctions smaller in magnitude can introduce an energy loss for holes, $\psi_h$, from P3HT. Native p-type metal oxide formation was studied for 3 different metals—Ag$_2$O/Ag, NiO/Ni, CuO/Cu. Oxides of Ag, Cu, and Ni have been shown to be of benefit to organic light emitting diodes (OLEDs) as well as OPVs. For comparison, MoO$_3$/Al, which is a common anode for inverted BHJ-OPVs, was studied.

Example 9

Calculation Methodology

Open-Circuit Voltage Calculation.

The maximum attainable $V_{oc}$ of a BHJ-OPV for a given donor-acceptor blend, $V_{oc,max}$, was given by:

$$V_{oc,max} = \frac{1}{q}(|E_{HOMO}^{inner}| - |E_{LUMO}^{acceptor}| - \Delta E) \quad (1)$$

where q was the elementary charge (in units of C), $E_{HOMO}^{donor}$ was the HOMO energy level of the donor, $E_{LUMO}^{acceptor}$ was the LUMO energy level of the acceptor, and $\Delta E$ is an empirical factor equal to 0.3 eV for P3HT: PCBM. The physical significance of $\Delta E$ was related either to the combination of the reverse dark current of the photodiode and the field-driven photocurrent BHJ-OPVs, or the exciton binding energy. For ohmic contacts at both the anode and cathode, the $V_{oc}=V_{oc,max}$ because there was no energy losses due to energy level mismatches. In the case of non-ohmic contacts, however, the $V_{oc}$ was reduced by an amount proportional to the energy loss for electrons and/or holes, $\psi_{e/h}$, at the respective electrodes:

$$V_{oc} = \frac{1}{q}(|E_{HOMO}^{inner}| - |E_{LUMO}^{acceptor}| - \Delta E - S_c\psi_e - S_a\psi_h) \quad (2)$$

where $S_{c/a}$ were the slope parameters for the dependence of $V_{oc}$ on cathode/anode work function. The slope parameter, S, was a measure of the strength of the interaction between the organic layer and the electrode. A strong interaction between the organic layer and the electrode occurred due to the formation of an interface dipole between the two layers, which was highly dependent on the identity of the two materials, the properties of their interface, and the method of depositing one material on the other. For BHJ-OPV devices, the S-parameter represented the $V_{oc}$ dependence on metal work function; however, S-parameters have also been defined for organic films on varying substrates, where the S-parameter represents the dependence of the effective work-function of the organic-coated substrate on the work function of the bare substrate. Both the S-parameter for devices and that for films were measures of the energy level alignment of the organic molecular orbitals and the underlying substrate Fermi level. The stronger the interface dipole, the lower the S-parameter value, which has been shown to be as small as 0.1 for non-ohmic contacts. The typical metal-insulator-metal (MIM) model that was used previously to calculate $V_{oc}$ assumed that there is no interface dipole formed, and that $V_{oc}$ depended linearly on the metal work function, with an S-parameter of 1; this should occur in the case of vacuum-level alignment, or the Mott-Schottky limit. In the case of ohmic contacts, it was shown that there was no dependence of $V_{oc}$ on metal work function, regardless of the workfunction of the metal, a process which has been referred to as 'Fermi level pinning'. Therefore, in the pinning regime, the S-parameter was zero. The S-parameter for non-ohmic contacts was cited as 0.1, 0.26, 0.6, and 1.0. The $V_{oc}$ was thus calculated for an S-parameter of 1.0, which assumed no interface dipole formation, as well as for an S-parameter of 0.1, which assumed formation of a strong interface dipole for non-ohmic contacts. For ohmic contacts, an S-parameter of 0 was used.

Ohmic contact occurred between the cathode and the n-type acceptor material when the magnitude of the workfunction of the cathode, $\phi_{c+}$, is less than or equal to $|E_{LUMO}^{acceptor}|$, due to Fermi level pinning, and $\psi_e=0$. For non-ohmic contact between the cathode and the acceptor, $|\phi_c|>|E_{LUMO}^{acceptor}|$, there was an energy loss for electrons at the cathode defined as:

$$\psi_e=|\phi_c|-|E_{LUMO}^{acceptor}| \quad (3)$$

For the case where the magnitude of the work-function of the anode, $\phi_a$ was greater than or equal to $|E_{HOMO}^{donor}|$, an ohmic contact was formed to the p-type donor material due to Fermi level pinning and $\psi_h=0$. For $|\phi_a|<|E_{HOMO}^{donor}|$ there was an energy loss for holes at the anode, which we define as:

$$\psi_h=|E_{HOMO}^{donor}|-|\phi_a| \quad (4)$$

The $V_{oc}$ was then calculated assuming that $|E_{HOMO}^{donor}|$ of P3HT was 5.0 eV, $|E_{LUMO}^{acceptor}|$ of PCBM was 4.0 eV, and $\Delta E$ for P3HT:PCBM was 0.3 eV.

Fill Factor Calculation.

The ideal fill factor ($FF_0$) which assumes ideal shunt and series resistances (i.e., shunt resistance→∞; series resistance→0), was calculated as follows:

$$FF_0 = \frac{v_{oc} - \ln(v_{oc} + 0.72)}{v_{oc} + 1} \quad (5)$$

where $V_{oc}$ was the normalized open-circuit voltage defined as:

$$v_{oc} = V_{oc}\left(\frac{q}{n_d k_B T}\right) \quad (6)$$

where $n_d$ is the diode ideality factor, $k_B$ is the Boltzmann constant, and T is temperature. If non-zero series resistances were present, the series fill factor ($FF_s$) was calculated as:

$$FF_s = FF_0(1 - 1.1r_s) + \frac{r_s^2}{5.4} \quad (7)$$

where $r_s$ was the normalized series resistance defined as:

$$r_s = \frac{R_s}{V_{oc}/J_{sc}} \quad (8)$$

where $R_s$ was the specific series resistance (in units of Ωcm²). Finally, when finite shunt resistances were considered, the total fill factor (FF) was calculated as:

$$FF = FF_s\left(1 - \frac{v_{oc} + 0.7}{v_{oc}} \frac{FF_s}{r_{sh}}\right) \quad (9)$$

where $r_{sh}$ is the normalized shunt resistance defined as:

$$r_{sh} = \frac{R_{sh}}{V_{oc}/J_{sc}} \quad (10)$$

Where $R_{sh}$ was the specific shunt resistance (in units of Ωcm²). Equations (5), (7), and (9) were accurate to less than a few percent for $v_{oc}$>10 and $r_{s+}1/r_{sh}$<0.4. Values of $n_d$ for P3HT:PCBM BHJ-OPVs were taken from the literature and averaged. $R_s$ values were obtained for both P3HT:PCBM BHJ-OPV devices containing PEDOT:PSS hole transport layers (conventional) and ZnO electron transport layers (inverted). Here, $n_d$=1.83, $R_s$=4.51 Ωcm² for conventional devices, $R_s$=5.36 Ωcm² for inverted devices, and room temperature (300 K) operation was assumed. Shunt resistance values varied considerably in the literature, but for well-optimized BHJ-OPVs, $R_{sh}$=1 Ωcm² is a typical value. Tabulated values of FF, $FF_s$, $FF_0$, the normalized parameters and literature values for the equivalent circuit parameters can be found in the SI.

Short-Circuit Current Density Calculation

The $J_{sc}$ was related to the efficiency of absorption of photons by the active layer (optical properties), as well as the efficiencies of separation and transport of the electrons and holes to their respective electrodes (electrical properties). The $J_{sc}$ depended on the external quantum efficiency, $\eta_{EQE}$, of the device as follows:

$$J_{sc} = q\int_\lambda \eta_{EQE}(\lambda) N_{ph}(\lambda) d\lambda \quad (11)$$

where λ is the wavelength (in units of nm) and $N_{ph}$ is the photon flux density of the AM 1.5 solar spectrum over the wavelength range of interest (in units of photons m⁻² nm⁻¹ s⁻¹). The $\eta_{EQE}$, which is defined as the ratio of the number of free carriers collected at the electrodes to the number of photons incident on the device, is determined by the product of the individual quantum efficiencies of each step of the conversion process of photons to electrons. Here, we approximate the $\eta_{EQE}$, to be given by:

$$\eta_{EQE}(\lambda) \approx \eta_a(\lambda) \quad (12)$$

where $\eta_a$ is the efficiency of photon absorption. By making this approximation, we have assumed that each photogenerated exciton has dissociated into free charge carriers, each of which have been collected at the respective electrode. While this effectively neglects the electrical transport aspects of the devices, e.g., by assuming an internal quantum efficiency ($\eta_{IQE}$) value of 100%, there is not expected to be a notable change in the efficiency of charge transport within the active layer for devices having different metallic electrodes, particularly since the generation rate maxima are located in nearly the same spatial position of the active layer for each electrode. Further, since the calculations in this work were carried out on a discrete basis, the integral in Eq. (11) becomes a summation:

$$J_{sc} = q\sum_\lambda (\eta_a(\lambda) N_{ph}(\lambda) d\lambda) = q\sum_\lambda \left(\eta_a(\lambda) \frac{I_{solar}(\lambda)}{h\nu} d\lambda\right) \quad (13)$$

where the photon flux density has been evaluated as the power density of light from the AM 1.5 solar spectrum, $I_{solar}$ (in units of W m⁻² nm⁻¹) divided by the energy per incident photon (hv, where h is Planck's constant (in units of J s photon⁻¹) and v is the frequency of light (in units of s⁻¹)). From Eq. (13), it is clear that in order to calculate the $J_{sc}$ of BHJ-OPV devices (assuming good electrical transport through the active layer), it is necessary to calculate $\eta_a$, the efficiency of photon absorption by the active layer.

The $\eta_a$ is related to the power density absorbed in the active layer, $I_{active}$ (W m⁻² nm⁻¹), by dividing it by the incident power density, $I_{solar}$:

$$\eta_a = \frac{I_{active}(\lambda)}{I_{solar}(\lambda)} \quad (14)$$

where $I_{active}$ is given by:

$$I_{active}(\lambda) = \sum_\lambda^{thickness} Q(z,\lambda) \cdot dz = \sum_z^{thickness} \alpha n I_{solar} \left|\frac{E(z,\lambda)}{E_0}\right|^2 \cdot dz \quad (15)$$

where Q is the thickness- and wavelength-dependent power absorbed by the active layer and is summed over the thickness of the active layer to determine the total power density absorbed by the active layer, α is the absorption coefficient of the active layer (in units of cm$^{-1}$, see Eq. (16)), n is the real part of the complex index of refraction, and $|E/E_0|^2$ is the normalized electric field intensity in the active layer. The absorption coefficient is related to the imaginary part of the complex index of refraction, k $$\alpha = \frac{4\pi k}{\lambda} \quad (16)$$

By inserting Eqs. (14) and (15) into (13), the $J_{SC}$ can be expressed as:

$$J_{sc} = q \sum_{\lambda}^{solar} \sum_{z}^{thickness} \left( \alpha n \left| \frac{E(z, \lambda)}{E_0} \right|^2 \frac{I_{solar}(\lambda)}{hv} dz d\lambda \right) \quad (17)$$

$$J_{sc} = q \sum_{\lambda}^{solar\,thickness} \sum_{z} \left( \frac{Q(z, \lambda)}{hv} dz d\lambda \right) \quad (18)$$

$$J_{sc} = q \sum_{\lambda}^{solar\,thickness} \sum_{z} (G(z, \lambda) dz d\lambda) \quad (19)$$

where G is the generation rate of excitons in the active layer and is equal to Q/hv, or the power absorbed by the active layer divided by the energy of an incident photon. As seen from Eq. (17), based on the assumptions made here, the $J_{SC}$ is primarily determined by the optical constants (n and k) and the electric field intensity within the device. Due to the nature of thin films, there is coherent interference that occurs within each layer of the device, since the thickness of each layer is on the order of or less than the wavelength of light, so the electric field intensity will vary greatly with changing thickness of each layer. As such, the thicknesses of ITO, the metal electrode, and the metal oxide coatings (when present) were fixed, but the thicknesses of the active layer and front IFL were optimized.

Efficiency Calculation.

The overall power conversion efficiency, $\eta_p$, was calculated using the following equation:

$$\eta_P = \frac{J_{sc} V_{oc} FF}{I_{solar}} \times 100\%. \quad (20)$$

Example 10

Computational Methodology

Electric Field Calculations/Simulation Parameters.

Full-field electromagnetic calculations were performed numerically using commercially available finite-difference time domain (FDTD) software for all of the devices studied here. The FDTD method was preferred over the traditional transfer matrix (TM) method because, although the TM method is good for studying planar thin films, it cannot be used to study effects such as non-homogenous active layer morphologies, scattering from rough surfaces, or confinement of the electric field from nanophotonic structures; however, we do not consider these factors in this study. Numerical techniques such as the FDTD method are useful for studying these structures, some of which are the subject of on-going work. In the simulations, plane wave excitation incident normal to the plane of the device was employed in all cases. Similar to the TM method, the FDTD method assumes that optical materials are non-magnetic (relative permeability, $\mu_r=1$) such that the only necessary data to input into the software are the optical constants, n and k (or equivalently the dielectric function, $\in = \in_1 + i\in_2$) of each material, and the dimensions of each layer and nanostructure. However, there are a number of simulation parameters that must be considered to ensure accurate results are achieved, e.g. the size of the mesh, the properties of the source, and the boundary conditions. In order to verify the accuracy of the FDTD simulations, initial simulations were compared to results obtained using the TM calculations, which were shown to agree to within 1%.

The FDTD method cannot be used practically for nanometer-scale objects distributed on the macro or millimeter scale due to limited computational resources; it is primarily used for structures of nano- or micrometer size. As such, the glass substrate is not included in the device, but the background index through which the electromagnetic source initially propagates is set to that of $SiO_2$ glass (n=1.52). The final result is then corrected for reflective losses at the air-glass interface from multiple passes through the device stack by multiplying the numerically calculated electric field value by the transmission coefficient at the glass-ITO interface as calculated by the TM methods.

The thickness of the remaining layers were set to the values previously described. Each layer had a cross-sectional area that was 'infinite' in extent by defining appropriate boundary conditions; see below. The FDTD simulation region cross-sectional area was set to 20 nm×20 nm with a depth of 1700 nm. The source was a plane wave pulse, with continuous wave normalization (CWN), a pulselength of 2.325 fs, wavelength range of 350-800 nm, and wavelength stepsize of 1 nm. The solar irradiance AM 1.5 spectrum was taken into consideration during post-simulation processing (see. Eq. (17)). As such, the source had an amplitude of 1, phase of 0°, and the polar and azimuthal angles were both also set to 0° (normal incidence). The source propagated in the direction normal to the device (z) with the electric field vector (E) polarized along the x direction and the magnetic field vector (H) polarized along the y direction. The source was 1000 nm from the first layer of the device. A two-dimensional frequency-domain field and power monitor as well as a 2D refractive index monitor were included in the simulation (in the x-z plane at y=40). The geometries of these monitors were identical and chosen to agree with the polarization of the plane wave source; the monitors extended beyond the simulation region in the x and z directions.

The boundary conditions of the simulation were as follows: anti-symmetric boundary conditions along the polarization direction of the E-field (x), symmetric boundary conditions along the polarization of the H-field (y), and perfectly matched layer (PML) boundary conditions along the direction of propagation (z), with 12 PMLs. Symmetry was enabled on all boundaries, and the structure was extended through the PMLs. The simulation time was 1000 fs. The simulations had a mesh accuracy set to 8, with mesh refinement type set to conformal variant 1. A mesh override of dx=dy=d=0.9 nm was set through the entire device. The simulations automatically shut-off when the normalized field intensity decays to less than $10_{-7}$.

Example 11

Optical Constants

For the simulations, the wavelength-dependent complex index of refraction ($\tilde{n}=n+ik$) of each layer of the device (metal, active layer, interface layers, transparent conducting electrode, glass) were required. SiO$_2$ was assumed to have a constant n of 1.52 throughout the visible spectrum and a constant k of 0 in order for the TM calculations to match the FDTD calculations (in the latter the background index must be set to a constant value (1.52)).

In order to simulate the electric field profile using Lumerical FDTD Solutions, the optical constants must be fit to a polynomial equation, which is optimized in the software itself. The input values into these fitting routines were 50 linearly spaced optical data points in the wavelength range of 350-800 nm. After the data were fitted, the polynomials were used in the software to obtain n and k at each wavelength between 350 and 800 nm (451 total wavelength points). This fitted discrete data was then exported from Lumerical to be used in the TM method calculations such that complex index of refraction of each layer was as similar as possible for the two methods of calculating the electric field profile were as similar as possible.

Example 12

Thickness Optimization

The front interface layer (PEDOT:PSS) and the active layer (P3HT:PCBM) for a conventional BHJ-OPV device were optimized by fixing the thicknesses of the other layers, and using a bare Al cathode, then performing FDTD simulations for 5 different PEDOT:PSS thicknesses (ranging from 10 to 50 nm, in 10 nm intervals), each having 12 different P3HT:PCBM thicknesses (ranging from 20 to 240 nm, in 20 nm intervals). The J$_{SC}$ was calculated for each simulation and an oscillatory-type behavior was observed for changing P3HT:PCBM thickness, as observed for others in the literature. The optimized thicknesses of the PEDOT:PSS and P3HT:PCBM layers were 10 nm and 240 nm, respectively.

Example 13

Calculations

Open-Circuit Voltage.

In the case of a p-type coating on the cathode as well as an n-type coating on the anode, the V$_{oc}$ was assumed to be zero, since they should serve as effective electron and hole blocking layers, respectively. The presence of strong interface dipoles (S$_c$ or S$_a$=0.1 at the cathode or anode of the conventional or inverted devices, respectively), which may form for strongly interacting layers, reduced the energy loss for charge collection ($\psi_e$ or $\psi_h$) at the respective electrodes, and increased V$_{oc}$. With optimized work-functions (i.e., ohmic contacts at both the cathode and anode), maximum attainable open-circuit voltage (V$_{oc,max}$) values of 0.7V were calculated for both conventional and inverted P3HT:PCBM BHJ-OPV devices (which is in good agreement with the design rules developed by Scharber et al., assuming a LUMO energy for PCBM of 4.0 eV and a HOMO energy of P3HT of 5.0 eV).

For conventional devices, V$_{oc}$ was negligible for S$_c$=1 when $|\phi_c| \geq |E_{LUMO}^{acceptor}|+qV_{oc,max}$, since the electron energy loss at the cathode exceeded the total V$_{oc}$. For inverted devices, V$_{oc}$ was also negligible for S$_a$=1 when $|\phi_a| \leq |E_{HOMO}^{donor}|-qV_{oc,max}$ V$_{oc,max}$ again due to the hole energy loss at the anode exceeding the total V$_{oc}$. For conventional devices, with increasing metal electrode workfunction, the Voc decreased from its maximum value to 0.585 V for S$_c$=0.1 and to 0 V for S$_c$=1 for the highest workfunction metals (Ni, Pd, Au). For inverted devices, with increasing bare/coated metal electrode work-function, the V$_{oc}$ increased to its maximum value from 0.47 V for S$_a$=0.1 and from 0 for S$_a$=1 for the lowest workfunction bare metals (Ba/Al, Ca/Al, Mg/Ag). The best performing cathodes for the conventional configuration were composed of the unstable low workfunction metals (i.e., LiF/Al, Ba/Al, Ca/Al, and Mg/Al) and for the inverted configuration were anodes with native metal oxide coatings (i.e., Ag$_2$O/Ag, NiO/Ni, and CuO/Cu), the stable high workfunction metals (Au, Pd, and Ni) and the standard inverted BHJ-OPV anode (i.e., MoO$_3$/Al).

Fill Factor.

The FF showed the same trends as V$_{oc}$ for both device configurations and the range of electrode materials studied, with maximum achievable values of 0.76 assuming no parasitic resistances (i.e., R$_s$=0, R$_{sh}$=∞). For V$_{oc}$=0, the FF$_0$ according to Eq. (5) results in a value of 0.33 due to the limited accuracy of the fill factor calculation for voc<10; however, a fill factor for V$_{oc}$=0 has no physical significance, so the FF$_0$ was set to 0 in these cases. Assuming no parasitic resistances, the maximum FF0 was identical for the conventional and inverted devices. However, the more meaningful calculation incorporating parasitic resistances resulted in reduced FF values, giving a maximum value for the FF of 0.70 for conventional devices and 0.68 for inverted devices. The main reason for this difference is the larger R$_s$ for ZnO-based BHJ-OPVs (5.36 Ωcm$^2$) compared to PEDOT:PSS-based devices (4.51 Ωcm$^2$). If the R$_s$ for inverted devices is set equal to or less than that of conventional devices, then the maximum FF for inverted devices can exceed that of conventional devices.

Optical Absorption Spectra and Short-Circuit Current Density.

Calculations of the optical absorption and J$_{sc}$ in the devices as a function of bare and coated metal electrode materials were performed to identify the electrodes with the most desirable optical response (i.e., low absorption loss) for the BHJ-OPV devices studied here. It was observed that Ag and Al electrodes resulted in the largest overall absorption in the active layer, with ~90% of light absorbed between 380 and 610 nm. For Au, Cu, Ba/Al, Pd, Ni, Ca/Al, and Mg/Ag electrodes, active layer absorption ranged from ~83% to 90% between 350 and 550 nm for the conventional configuration. Between 550 nm and 610 nm, devices with Au, Cu, and Ba/Al electrodes absorbed between 80 and 85% of light in the active layer, but for Pd, Ni and Ca/Al electrodes, active-layer absorption dropped to ~75-78%, and for Mg/Ag electrodes active-layer absorption dropped further to ~65-85%. All active layer absorption dropped rapidly to ~10% from 610 to 660 nm, then continued to drop towards 0% at longer wavelengths. For all metals, the absorption onset in the active layer occurred at 655±5 nm. Conventional and inverted active layer absorption spectra showed similar trends, except for an additional dip in the inverted fractional absorption spectra in the range 350-380 nm arising as a result of interband absorption from the ZnO ETL.

The metals that were more absorptive in the visible part of the spectrum tended to be poorer reflectors, which reduced the overall active layer absorption. Both Ag and Al had low absorption loss in the range of 350-600 nm (Ag absorbed between <1 and 2% and Al absorbed between <1 and 5%). Although Al became more absorptive at longer wavelengths, with absorption ranging from 5% to 18% between 600 and 800 nm, this did not significantly impact the amount of light absorbed by the active layer since P3HT does not absorb strongly beyond 650 nm. For lower bandgap polymers (such as PCDTBT (a polycarbazole derivative), PBDTT, or PTB7 (two benzodithiophene derivatives), longer wave-length absorption in Al electrodes may substantially reduce active layer absorption. Note that Ag absorbed less than 5% of light beyond 600 nm, making it more ideal for lower bandgap polymer absorbers. Copper and gold were both slightly more absorptive at shorter wavelengths, absorbing ~7% and 9%, respectively, at 390 nm, and, overall, absorbing up to 7% and 5% of light between 350 and 600 nm, respectively. This is attributed to interband absorption by Cu and Au in the range of 500-600 nm. This region corresponded to the region of maximum absorption by P3HT:PCBM, which resulted in Au- or Cu-based electrodes reflecting less light (between 350 and 600 nm) back into the active layer compared with Ag- or Al-based electrodes. Although Cu and Au were less absorptive beyond 600 nm (5-7% for Cu and 6-10% for Au), P3HT does not absorb strongly beyond 650 nm, so the lower loss at longer wavelengths did not compensate the high loss at shorter wavelengths.

The remaining metals all followed a similar trend of absorbing less incident light in the region of 350-600 nm (where most of the light was absorbed by P3HT:PCBM) and absorbing much more beyond 600 nm. At 390 nm, the total light absorbed in the metal was 4.4%, 6.0%, 6.6%, 8% AND 10% FOR Ba/Al, Pd, Ca/Al, Ni and Mg/Ag, respectively. Beyond 600 nm, the absorption of these metals peaked near 650 nm, where the fraction of light absorbed by each metal was 31%, 40%, 48%, 53%, and 69% for Ba/Al, Pd, Ni, Ca/Al, and Mg/Ag, respectively. The low workfunction metals, Ba, Ca, and Mg, all tended to have high absorption losses, and would more than likely have exceeded the absorption losses in Pd and Ni if a comparable thickness was used for the low workfunction metals (200 nm). It should be noted that thicknesses reported in the literature for Ca range up to 50 nm-80 nm, which would result in even greater parasitic absorption. Fractional absorption in the metal layer was similar for both conventional and inverted device configurations, except for a dip in metal layer absorption between ~350 and 380 nm, as described above. Less than 1% of the total (integrated) light was absorbed by each of the 2-nm-thick metal oxide/fluoride layers.

It was observed that the amount of light absorbed by the active layer increased with decreasing fraction of light absorbed by the metal (i.e. increasing reflectivity of the metal electrode) with the exception of NiO/Ni, Al and all metal oxide/fluoride-coated Al electrodes. Inverted devices tended to absorb more light in the active layer compared with conventional devices. It was observed that the $J_{sc}$ increased as the fraction of light absorbed in the active layer increased, but did not correlate with total absorbed light in the device (due to parasitic absorption in more absorptive metals such as Mg). In all cases, the $J_{sc}$ of inverted devices was larger than that of conventional devices by 0.12-0.19 mA/cm$^2$, with inverted devices reaching a maximum $J_{sc}$ of 14.26 mA/cm$^2$ for a Ag anode compared with 14.13 mA/cm$^2$ for a conventional device with a Ag cathode. This is attributed to the larger transmissivity of ZnO compared to PEDOT:PSS beyond 380 nm. Ag and Al electrodes, either bare or coated, resulted in the highest $J_{sc}$ values in both conventional or inverted configurations; devices employing the low workfunction bilayer metal electrodes, Ni, and Pd resulted in the lowest $J_{sc}$ values, with Mg/Ag having the lowest $J_{sc}$ of 12.66 mA/cm$^2$ in the inverted configuration. The difference between 1 (i.e., total normalized incident light intensity) and the total integrated fraction of light absorbed in each device represents the fraction of light lost due to reflection; thus, if light trapping techniques, such as application of anti-reflection coatings, are employed, then BHJ-OPVs with the lowest total absorption (i.e., Ag, Au, Cu metal electrodes) have the most potential for improvement.

Power Conversion Efficiency.

Low work-function metals (bare or coated) (e.g., LiF/Al, Ba/Al, Mg/Al) are necessary for high-efficiency conventional devices (efficiencies of up to 6.77% for LiF/Al); however, lower workfunction metals are typically not stable in air and are very likely to have relatively short operational lifetimes. Higher workfunction metal electrodes (e.g., Au, Pd, Ni), native metal oxide-coated metal electrodes (e.g., Ag2O/Ag, CuO/Cu, NiO/Ni), or high workfunction p-type metal oxide-coated metal electrodes (e.g., MoO$_3$/Al) are necessary for high-efficiency inverted devices (efficiency of up to 6.70% for Ag$_2$O/Ag) and are expected to be more stable in ambient conditions. It is notable that p-type native metal oxide formation, which is likely to occur for Ag, Cu, and Ni when exposed to air or if oxygen permeates through the device, can result in high-efficiency inverted devices, but is detrimental to conventional device, can result in high-efficiency inverted devices, but is detrimental to conventional device performance; therefore the performance of conventional devices is likely to degrade with aging or oxidation of the electrode.

While this invention has been described with an emphasis upon preferred embodiments, it will be obvious to those of ordinary skill in the art that variations in the preferred compositions and methods can be used and that it is intended that the invention can be practiced otherwise than as specifically described herein. Accordingly, this invention includes all modifications encompassed within the spirit and scope of the invention as defined by the claims that follow.

What is claimed is:

1. An organic optoelectronic device comprising: a substrate and a plurality of structures disposed thereon, said structures comprising: (a) a first electrode vertically separated from (b) a second electrode by (c) an electrode gap comprising an organic photoactive layer disposed within the gap, wherein one of the electrodes comprises a plurality of plasmonic metal nanostructures, wherein the nanostructures project towards the electrode gap and the metal is selected from the group consisting of gold, aluminum, silver, calcium, copper, and nickel; and an additional layer disposed in the electrode gap.

2. The organic optoelectronic device of claim 1, wherein the first electrode is an anode comprising a plurality of plasmonic metal nanostructures and is disposed closer to the substrate than the second electrode, which is a cathode.

3. The organic optoelectronic device of claim 2, wherein the metal is selected from the group consisting of gold, nickel, silver, and copper.

4. The organic optoelectronic device of claim 2, wherein the plurality of plasmonic metal nanostructures of one of the electrodes further comprises a native metal oxide coating layer.

5. The organic optoelectronic device of claim 4, wherein the native metal oxide coating layer is selected from the group consisting of CuO, NiO, Ag$_2$O, and Au$_2$O$_3$.

6. The organic optoelectronic device of claim 4, wherein the native metal oxide coating layer comprises a thickness from about 1 nm to about 5 nm.

7. The organic optoelectronic device of claim 1, wherein the first electrode is a cathode comprising a plurality of plasmonic metal nanostructures and is disposed closer to the substrate than the second electrode, which is an anode.

8. The organic optoelectronic device of claim 7, wherein the plurality of plasmonic metal nanostructures further comprises a metal oxide coating layer.

9. The organic optoelectronic device of claim 8, wherein the metal oxide coating layer is selected from the group consisting of ZnO and $TiO_2$.

10. The organic optoelectronic device of claim 1, wherein the plurality of nanostructures comprises a nanorod array, a nanocone array, a nanoparaboloid array, a nanoscale grating, or a nanopillar array.

11. The organic optoelectronic device of claim 1, wherein at least one of the nanostructures comprises a diameter ranging from about 10 nm to about 200 nm.

12. The organic optoelectronic device of claim 1, wherein at least one of the nanostructures comprises an aspect ratio ranging from about 0.3 to about 5.

13. The organic optoelectronic device of claim 1, wherein the organic photoactive layer comprises a conjugated organic polymer.

14. The organic optoelectronic device of claim 13, wherein the conjugated organic polymer is selected from the group consisting of poly(3-hexylthiophene) (P3HT); poly[N-9'-heptadecanyl-2,7-carbazole-alt-5,5-(4',7'-di-2-thienyl-2',1',3'-benzothiadiazole)] (PCDTBT); poly({4,8-bis[(2-ethylhexyl)oxy]benzo[1,2-b:4,5-b']dithiophene-2,6-diyl}{3-fluoro-2-[(2-ethylhexyl)carbonyl]thieno[3,4-b]thiophenediyl}) (PTB7); poly(9,9-di-n-octylfluorenyl-2,7-diyl) (PFO); poly[(9,9-di-n-octylfluorenyl-2,7-diyl)-alt-(benzo[2,1,3]thiadiazol-4,8-diyl)](F8BT); and poly[2-methoxy-5-(2-ethylhexyloxy)-1,4-phenylenevinylene] (MEH-PPV).

15. The organic optoelectronic device of claim 13 further comprising a fullerene derivative combined with a conjugated organic polymer absorber, wherein the fullerene derivative comprises phenyl-C61-butyric acid methyl ester ($PC_{60}BM$).

16. The organic optoelectronic device of claim 1, wherein the additional layer is selected from the group consisting of poly(3,4-ethylenedioxythiophene):poly(styrenesulfonate) (PEDOT:PSS); $MoO_3$; ZnO; and $TiO_2$.

17. An article comprising the organic optoelectronic device of claim 1, wherein the article is selected from the group consisting of an organic light-emitting diode, an organic solar cell, an optically pumped laser, and an indirectly electrically pumped laser.

* * * * *